United States Patent
Jones (10) Patent No.: US 8,424,399 B2
(45) Date of Patent: Apr. 23, 2013

(54) PROBE HOLDER ASSEMBLY FOR AN END TO END TEST OF ADHESIVES AND SEALANTS

(75) Inventor: Fatima Jones, Guilford, CT (US)

(73) Assignee: Covidien LP, Mansfield, MA (US)

( * ) Notice: Subject to any disclaimer, the term of this patent is extended or adjusted under 35 U.S.C. 154(b) by 300 days.

(21) Appl. No.: 12/898,985

(22) Filed: Oct. 6, 2010

(65) Prior Publication Data

US 2011/0100140 A1    May 5, 2011

Related U.S. Application Data

(60) Provisional application No. 61/256,047, filed on Oct. 29, 2009.

(51) Int. Cl.
*G01D 21/00* (2006.01)

(52) U.S. Cl.
USPC ........................................ 73/866.5

(58) Field of Classification Search .............. 73/866.5
See application file for complete search history.

(56) References Cited

U.S. PATENT DOCUMENTS

| 5,356,593 | A | 10/1994 | Heiberger et al. |
| 6,071,288 | A | 6/2000 | Carol et al. |
| 6,126,636 | A | 10/2000 | Naka |
| 7,362,115 | B2 | 4/2008 | Andrews et al. |
| 7,514,915 | B2 | 4/2009 | Dunklee |
| 2006/0030778 | A1 | 2/2006 | Mendlein et al. |
| 2006/0043257 | A1 | 3/2006 | Cheng et al. |
| 2006/0170441 | A1 | 8/2006 | Andrews et al. |
| 2006/0192574 | A1 | 8/2006 | Furukawa et al. |
| 2008/0102533 | A1 * | 5/2008 | Kim .............................. 436/147 |
| 2008/0296516 | A1 | 12/2008 | Tomimatsu et al. |
| 2009/0008578 | A1 | 1/2009 | Tomimatsu et al. |

FOREIGN PATENT DOCUMENTS

WO    99/08598    2/1999

OTHER PUBLICATIONS

Education-Mart Scientific Instruments Exporters, "Educational Laboratory Burette Stand & Clamps", Mar. 15, 2006.*

* cited by examiner

*Primary Examiner* — John Fitzgerald
*Assistant Examiner* — David Z Huang (57) ABSTRACT

A test assembly is provided having a platform with an indentation. A probe holder assembly is placed in the indentation of the platform. The probe holder assembly includes a base with an indentation configured to receive a tissue specimen, a plate configured to secure the tissue specimen to the base, and a probe holder configured to hold a probe in contact with an adhesive placed on the tissue specimen.

8 Claims, 7 Drawing Sheets

PROBE HOLDER ASSEMBLY FOR AN END TO END TEST OF ADHESIVES AND SEALANTS

CROSS REFERENCE TO RELATED APPLICATIONS

The present application claims priority to U.S. Provisional Application Ser. No. 61/256,047, filed Oct. 29, 2009, entitled "PROBE HOLDER ASSEMBLY FOR AN END TO END TEST OF ADHESIVES AND SEALANTS", the contents of which are hereby incorporated by reference in their entirety.

BACKGROUND

1. Technical Field

The present disclosure relates generally to a method and apparatus for testing adhesives and sealants. More particularly, the present disclosure is directed to a probe holder assembly adapted to perform an end to end test of adhesives and sealants.

2. Background of the Related Art

The use of adhesives and sealants are an important aspect of medical practice. They can be used for a variety of indications including, but not limited to, homeostatsis, hemostasis, wound closure and fistula repair that may be caused by trauma or a medical procedure. Medical adhesives or sealants are capable of bonding tissue surfaces together quickly while promoting or at least not inhibiting normal healing.

The American Society for Testing and Materials (ASTM) has developed a standard for testing properties of tissue adhesives in tension. ASTM F2258-05 entitled "Standard Test Method for Strength Properties of Tissue Adhesive in Tension", the contents of which are incorporated herein by reference, describes the procedure for testing medical adhesives and sealants. In the above mentioned standard, a tissue specimen is applied to a probe and another tissue specimen is secured to a base. The test adhesive or sealant is applied to the tissue specimen secured to the base and the probe is lowered into the adhesive or sealant. The adhesive or sealant is allowed to cure and then the probe is pulled back and the force is measured to determine the adhesive properties of the test material.

When an adhesive or sealant is applied, such adhesive or sealant tends to cure or harden at a rapid rate, sometimes instantaneously. As such, when a batch of the adhesive material is created, by the time the adhesive properties of the material have been tested using the above described standard, the batch has cured and a new batch has to be created to test the sample again. This has many disadvantages in that it increases the time needed to test the adhesives or sealants on different tissue specimens and each batch that is created may not be the same as a previous batch which may result in a wide range of values for the adhesive properties of the test material.

SUMMARY

The present disclosure relates to a test assembly used to test the mechanical properties of adhesives or sealants.

According to an embodiment of the present disclosure, a test assembly having a platform and a probe holder assembly is provided. The platform has an indentation and the probe holder assembly is configured to be placed in the indentation of the platform. The probe holder assembly includes a base having an indentation configured to receive a tissue specimen, a plate configured to secure the tissue specimen to the base, and a probe holder configured to hold a probe in contact with an adhesive placed on the tissue specimen.

In the test assembly, the plate is secured to the base with screws. The probe holder includes a post, a first arm having at least one through hole and a curved portion, and a second arm having at least one through hole and a curved portion. The first arm and the post may be formed from a single piece or the first arm may be removably coupled to the post. The first arm and second arm are secured together with screws.

According to another embodiment of the present disclosure, an apparatus for testing properties of adhesive or sealants is provided. The apparatus includes a platform having an indentation, a probe having a window, and a probe holder assembly configured to be placed in the indentation of the platform. The probe holder assembly includes a base having an indentation configured to receive a tissue specimen, a plate configured to secure the tissue specimen to the base, and a probe holder configured to hold the probe in contact with an adhesive placed on the tissue specimen. The apparatus also includes a grip having a hook portion configured to be inserted into the window of the probe and a distal portion configured to be inserted into an adaptor of a texture analyzer instrument. The hook portion of the grip has a protrusion configured to secure the probe in the hook portion of said grip.

According to another embodiment of the present disclosure, a test assembly is provided. The test assembly has a platform having a plurality of indentations and a plurality of probe holder assemblies. Each probe holder assembly is configured to be inserted into each indentation of the platform. Each probe holder assembly includes a base having an indentation configured to receive a tissue specimen, a plate configured to secure the tissue specimen to the base, and a probe holder configured to hold a probe in contact with an adhesive placed on the tissue specimen.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

As used herein, the term "specimen" refers to organic material such as tissue or inorganic material that may simulate tissue. Further, the term "distal" refers to that portion of the instrument, or component thereof which is further from the specimen while the term "proximal" refers to that portion of the instrument or component thereof which is closer to the specimen.

Figure 1:
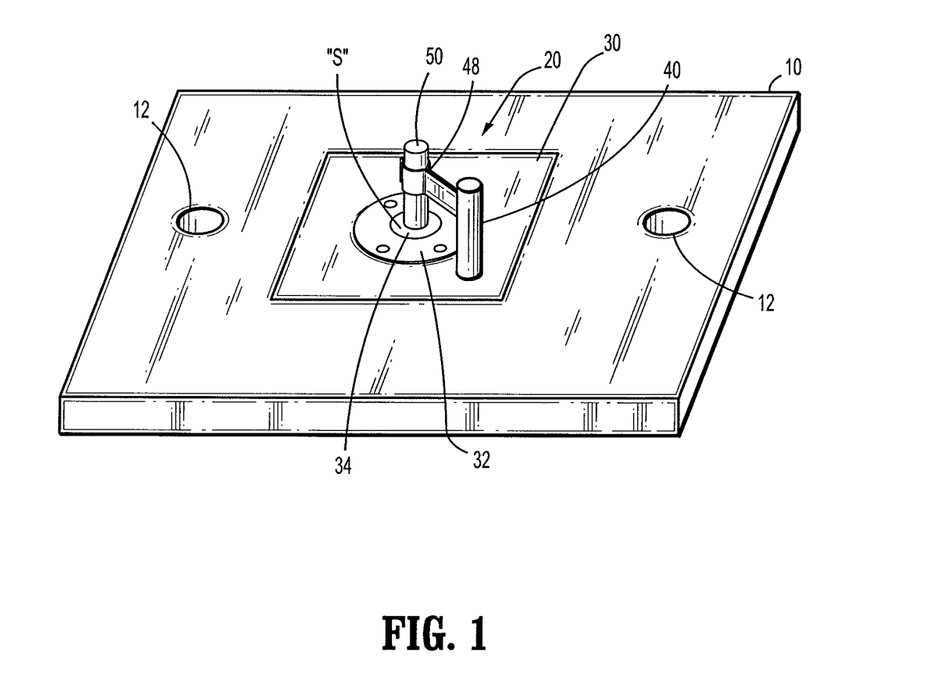
FIG. 1 is a perspective view of a test assembly in accordance with an embodiment of the present disclosure.
Figure 2:
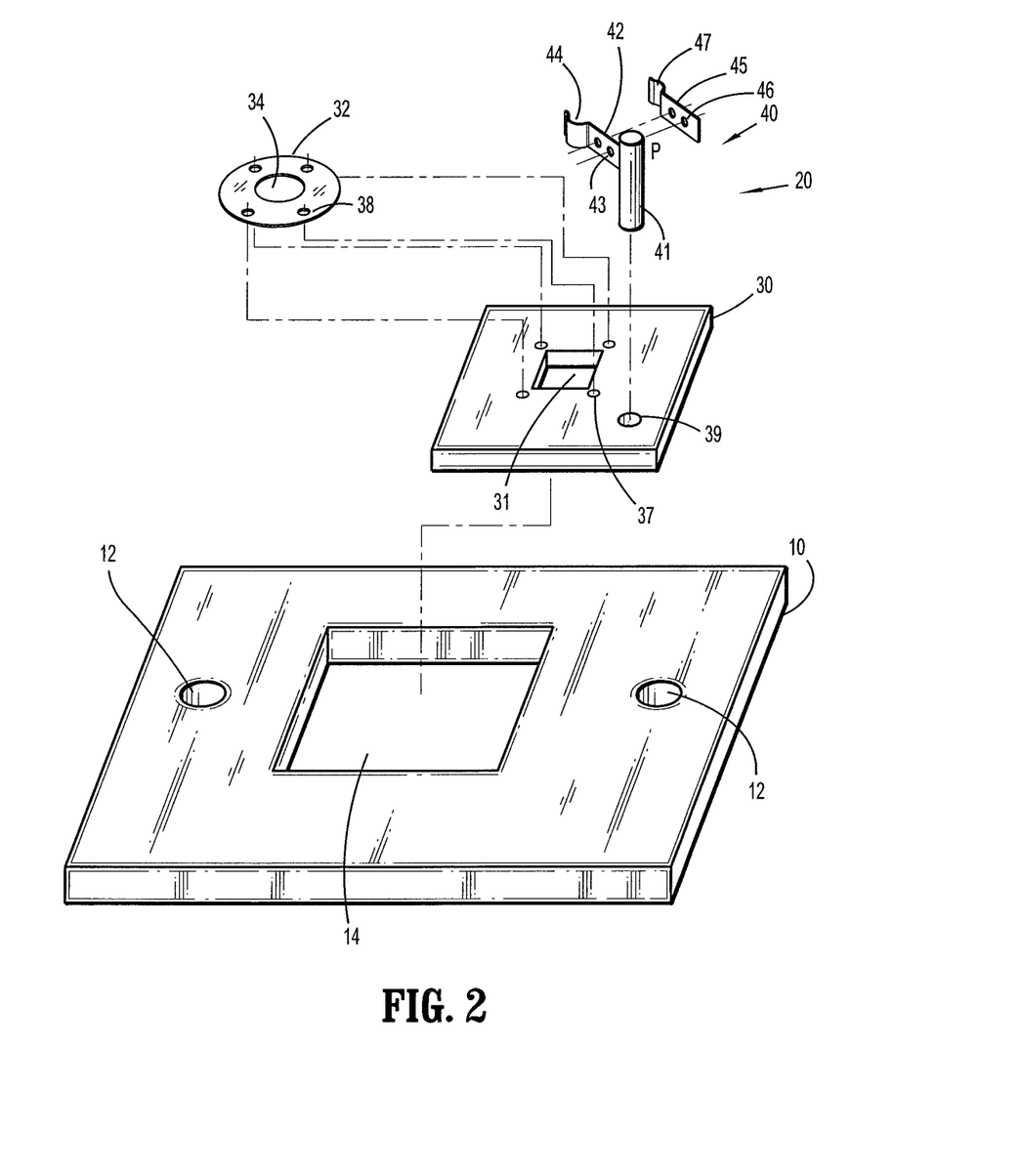
FIG. 2 is a perspective view with parts separated of a probe holder assembly in accordance with an embodiment of the present disclosure.

FIGS. 1 and 2 depict a test assembly in accordance with an embodiment of the present disclosure. As shown in FIG. 1, the test assembly has a rectangular platform 10 made of stainless steel. Although stainless steel is disclosed, other suitable materials are contemplated including but not limited to engineering metals and/or plastics. Platform 10 has a pair of openings or holes 12 that are used to secure platform 10 to a table or other working surface (not shown). Each opening 12 may be configured to receive a screw, bolt, or clamp to attach the platform 10 to the working surface or it may be configured to receive a protrusion or peg (not shown) from the working surface to secure the platform 10 to a working surface. An indentation 14 is provided in platform 10 to secure the probe holder assembly 20 in platform 10. In another embodiment, described hereinbelow, platform 10 may have multiple indentations to accommodate multiple probe assemblies in order to test different combinations of tissues and adhesives or sealants Although platform 10 is shown as having a rectangular shape, platform 10 may be formed as any circular or polygonal shape.

Probe holder assembly, generally shown as 20, includes a base 30 and probe holder 40. Base 30 has an indentation 31 where a user places a specimen "S". A round plate 32 having an opening 34 is placed over the specimen "S" and secured to base 30 by screws (not shown). Base 30 includes holes 37 which are aligned with holes 38 of plate 32. Holes 37 are threaded to receive screws (not shown) so that plate 32 is firmly secured to base 30. In one embodiment of the present disclosure, base 30 and plate 32 are made from stainless steel. Although plate 32 is shown as having a circular shape, other shapes may be utilized to secure the specimen in place.

As shown in FIG. 2, a hole 39 is provided to receive post 41 of probe holder 40. Hole 39 has a circular shape that corresponds to the circular shape of the post 42. The circular shape allows post 41 to rotate within hole 39 to position a probe 50 (FIG. 3) above the specimen "S". Probe holder 40 has an arm 42 and arm 45. Arm 42 is directly connected to post 41 at an angle perpendicular to a central axis "P" of post 42. Arm 42 and post 41 may be formed as a single piece or arm 42 may be removable from post 41. Arm 42 has through holes 43 and the proximal end of arm 42 has a semi circular curved portion 44. Arm 45 has through holes 46 and the proximal end of arm 45 has a semi circular curved portion 47. When arms 42 and 45 are placed together and holes 43 and 46 are aligned, an aperture 48 is defined by the curved portions 44 and 47 of arms 42 and 45 respectively. Probe 50, which will be described hereinbelow, is placed in aperture 48. Screws (not shown) are inserted through holes 43 and 46 to secure the probe in place.

Figure 3:
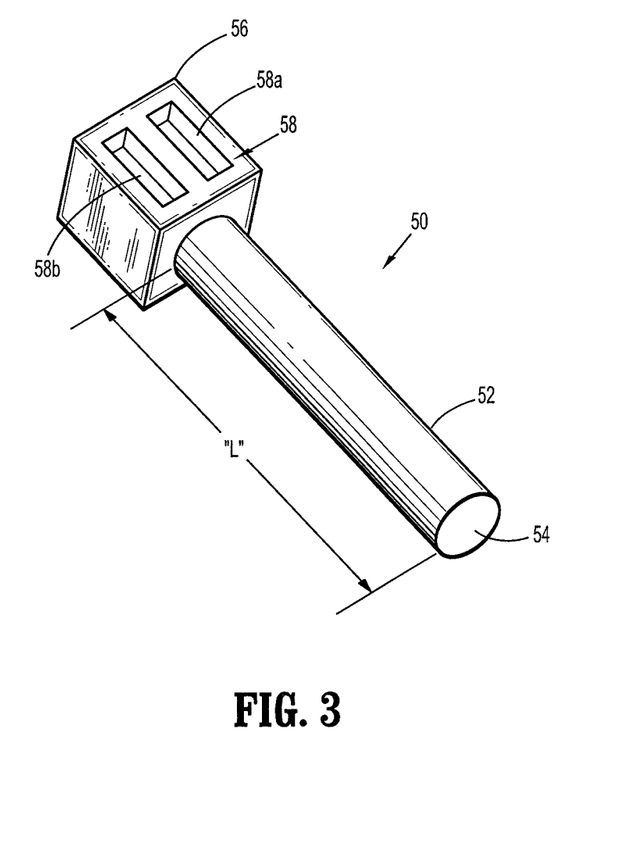
FIG. 3 is a perspective view of a probe in accordance with an embodiment of the present disclosure.
Figure 4:
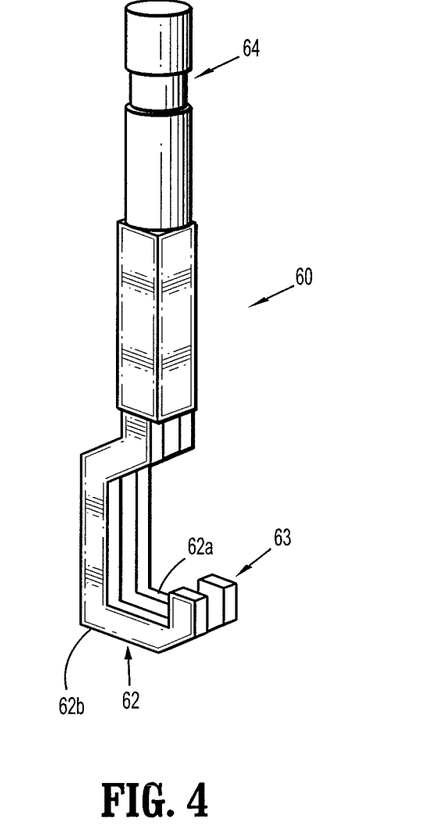
FIG. 4 is a perspective view of a grip in accordance with an embodiment of the present disclosure.
Figure 5:
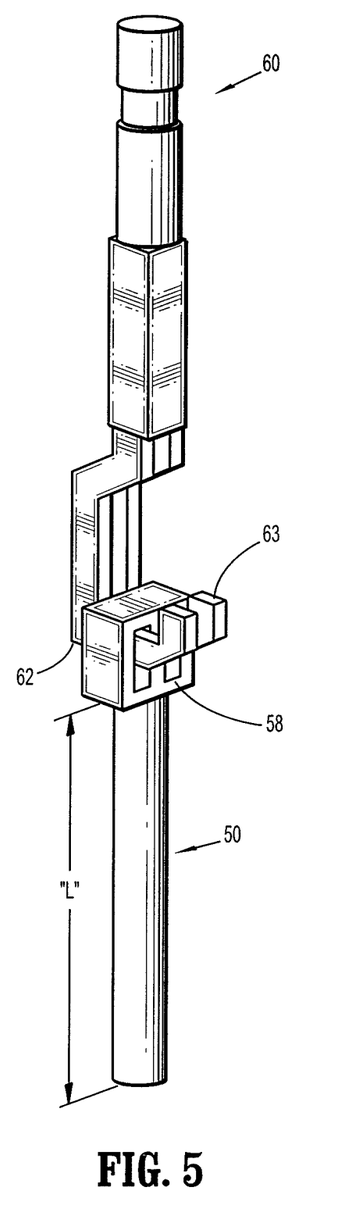
FIG. 5 is a perspective view of a probe coupled with a grip in accordance with an embodiment of the present disclosure.

Probe 50, as shown in FIG. 3, is made from stainless steel and has a cylindrical shape along length "L" of the probe. Proximal end 52 of probe 50 is circular in shape and presents a smooth surface 54 toward a specimen. The distal end 56 of probe 50 has window 58 that allows the probe 50 to be removably coupled to a grip 60 (FIGS. 4 and 5). Window 58 may be formed from a single aperture or, as shown in FIG. 3, having two apertures 58a and 58b.

Grip 60, as shown in FIG. 4, is composed of stainless steel and is designed to fit into existing replaceable adaptors for a texture analyzer instruments such as a TA57R probe. The proximal end of grip 60 has a hook portion 62 with a protrusion 63. Hook portion 62 corresponds to window 58 of probe 50 and is designed to be easily inserted into window 58. Hook portion 62 may be composed of a single hook or, as shown in FIG. 4, two hooks 62a and 62b which would correspond to apertures 58a and 58b respectively. The distal portion 64 of grip 60 fits into a replaceable adaptor (not shown) of a texture analyzer instrument. Grip 60 is universal in that the distal portion can fit into a variety of texture analyzer instruments with an adaptor. FIG. 5 depicts a probe 50 coupled to grip 60. As shown in FIG. 5, hook portion 62 of grip 60 fits into window 58 of probe 50. Protrusion 63 keeps probe 50 from sliding off of the hook portion 62.

Although probe holder assembly 20 has been described above as being secured to platform 10 by placing probe holder assembly 20 in indentation 14, other methods of securing probe holder assembly 20 to platform 10 are possible. For example, after probe holder assembly 20 is assembled, which includes coupling base 30, probe holder 40 and probe 50 together as described above, the completed probe holder assembly 20 is coupled to grip 60 by sliding window 58 into hook portion 62. Probe holder assembly 20 may then be secured to platform 10 using one or more clamps (not shown) that may be removably coupled to platform 10. Alternatively, probe holder assembly 20 may be magnetically coupled to platform 10.

Figure 6:
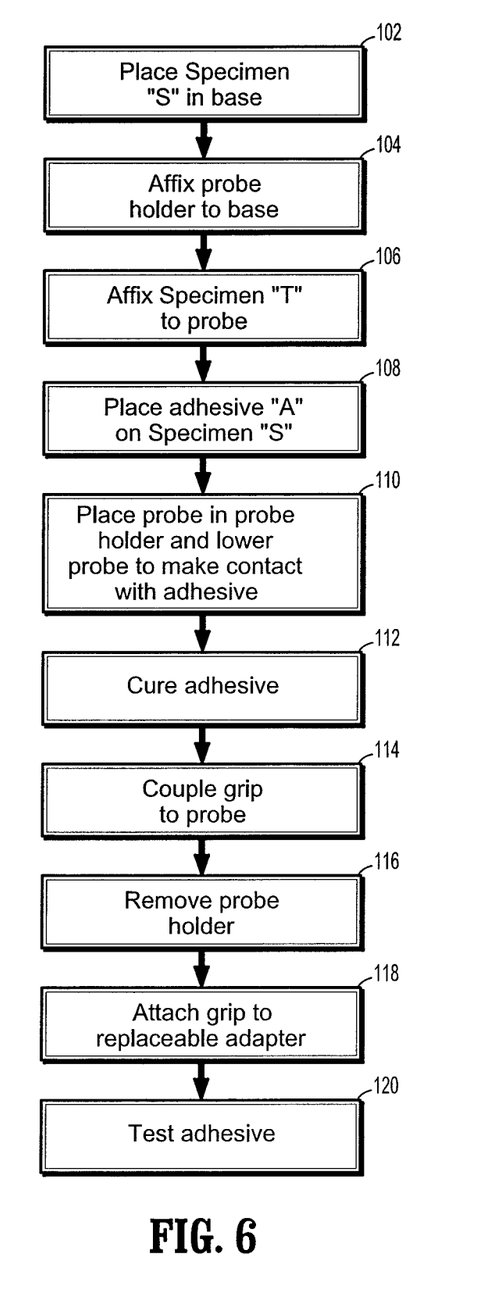
FIG. 6 is a flow chart of a tensile test method in accordance with an embodiment of the present disclosure.

The procedure for testing the tensile strength of an adhesive or sealant is described with reference to FIG. 6. As shown in FIG. 6, the procedure begins in step 102 when a user places a specimen "S" in indentation 31 of base 30 and is secured in place by plate 32. In step 104, probe holder 40 is assembled by aligning holes 43 and 46 of arms 42 and 45 and placing screws in holes 43 and 46. Post 41 of probe holder 40 is placed in hole 39 of base 30. In step 106, another piece of specimen "T" is affixed to surface 54 of probe 50. Specimen "T" is secured to surface 54 by double sided tape or a strong adhesive such as cyanoacrylate. In step 108, a test adhesive or sealant "A" is placed in the center of specimen "S". In step 110, the probe 50 is placed in aperture 48 and lowered until specimen "T" makes contact with test adhesive or sealant "A". Test adhesive or sealant "A" is allowed to cure in step 112. Once test adhesive or sealant "A" has cured, hook portion 62 of grip 60 is placed in window 58 of probe 50 in step 114. In step 116, probe holder 40 is disassembled so that probe holder 40 does not impart any forces on the probe during the testing of the adhesive or sealant. In step 118, grip 60 is attached to the replaceable adaptor of the texture analyzer instrument. The tensile strength of test adhesive or sealant "A" is tested in step 120.

Figure 7:
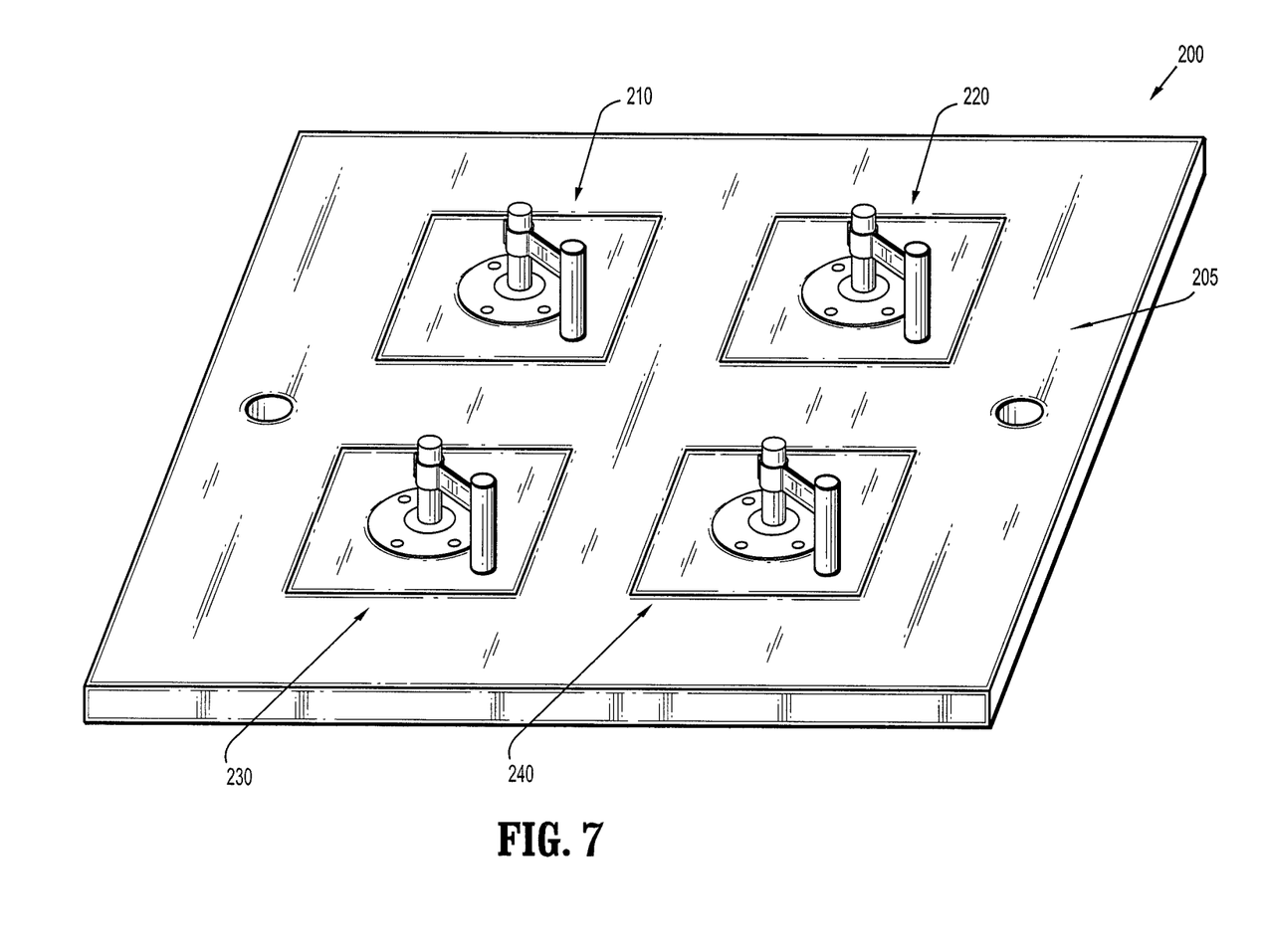
FIG. 7 is a perspective view of a test assembly in accordance with embodiments of the present disclosure.

Although the above description describes a test assembly having a single probe holder assembly, the test assembly may incorporate multiple probe holder assemblies as show in FIG. 7. FIG. 7 depicts a test assembly 200 having four probe holder assemblies 210, 220, 230 and 240. Because the adhesive or sealants being tested tend to cure rapidly, it would be advantageous to set up multiple tests at once so that the adhesive or sealant does not have to be created after each test. This would reduce the amount of time needed to test the adhesive or sealant on multiple specimens. For instance, each probe holder assembly 210, 220, 230 and 240 may have a different specimen secured therein. A batch of the test adhesive or sealant would be created and applied to each specimen and the test adhesive or sealant on each probe holder assembly would cure in substantially the same amount of time. Additionally, a multiple probe holder can be utilized to secure the transportation of samples to a humidity chamber or heat oven.

Alternatively, a user may want to test different adhesives or sealants on the same specimen. If a user had to set up one test at a time, the time it would take to complete the testing would be great. Therefore, it would be advantageous to set up multiple tests at once so that the different adhesives or sealants can cure during the same time period and would not have to be repeated after each test. This would reduce the amount of time needed to test the multiple adhesives or sealants on the specimen. For instance, each probe holder assembly 210, 220, 230 and 240 would have a specimen secured therein. Different test adhesives or sealants would be created and each adhesive or sealant would be applied to a specimen on separate probe holder assemblies thereby reducing the amount of time needed to set up the test procedure.

Although, FIG. 7 shows a rectangular platform 205 having four probe holder assemblies, platform 205 may take any shape that would accommodate any number of probe holder assemblies.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

The invention claimed is:

1. An apparatus for testing properties of adhesive or sealants, said apparatus comprising:

a platform having an indentation;

a probe having a window;

a probe holder assembly configured to be placed in the indentation of said platform, said probe holder assembly having a base having an indentation configured to receive a tissue specimen, a plate configured to secure the tissue specimen to said base, and a probe holder configured to hold said probe in contact with an adhesive placed on the tissue specimen; and a grip having a hook portion configured to be inserted into the window of said probe and a distal portion configured to be inserted into an adaptor of a texture analyzer instrument.

2. The apparatus according to claim 1, wherein said plate is secured to said base with screws.

3. The apparatus according to claim 1, wherein said probe holder comprises:

a post;

a first arm having at least one through hole and a curved portion; and a second arm having at least one through hole and a curved portion.

4. The apparatus according to claim 3, wherein said first arm and said post are formed from a single piece.

5. The apparatus according to claim 3, wherein said first arm is removably coupled to said post.

6. The apparatus according to claim 3, wherein the first arm and second arm are secured together with screws.

7. The apparatus according to claim 1, wherein said hook portion of said grip has a protrusion configured to secure the probe in said hook portion of said grip.

8. The apparatus according to claim 1, wherein the platform has a plurality of indentations and a plurality of probe holder assemblies, each probe holder assembly configured to be inserted into each indentation of said platform.

* * * * *